(12) United States Patent
Basheer et al.

(10) Patent No.: US 10,191,061 B2
(45) Date of Patent: Jan. 29, 2019

(54) MICROWAVE-ASSISTED HEADSPACE LIQUID-PHASE MICROEXTRACTION OF AN ANALYTE

(71) Applicant: KING FAHD UNIVERSITY OF PETROLEUM AND MINERALS, Dhahran (SA)

(72) Inventors: Chanbasha Basheer, Karimangalam (IN); Abdulnaser Khaled Alsharaa, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 177 days.

(21) Appl. No.: 15/234,694

(22) Filed: Aug. 11, 2016

(65) Prior Publication Data
US 2017/0052191 A1 Feb. 23, 2017

Related U.S. Application Data

(60) Provisional application No. 62/207,756, filed on Aug. 20, 2015.

(51) Int. Cl.
| | |
|---|---|
| *G01N 33/64* | (2006.01) |
| *G01N 1/44* | (2006.01) |
| *G01N 33/50* | (2006.01) |
| *G01N 30/06* | (2006.01) |
| *G01N 1/40* | (2006.01) |

(52) U.S. Cl.
CPC .......... *G01N 33/64* (2013.01); *G01N 1/4005* (2013.01); *G01N 1/44* (2013.01); *G01N 30/06* (2013.01); *G01N 33/50* (2013.01); *G01N 2001/4016* (2013.01); *G01N 2333/405* (2013.01); *G01N 2333/4603* (2013.01); *G01N 2560/00* (2013.01)

(58) Field of Classification Search
None
See application file for complete search history.

(56) References Cited

U.S. PATENT DOCUMENTS

| | | | |
|---|---|---|---|
| 7,231,806 B2 | 6/2007 | Jen | |
| 7,468,281 B2 | 12/2008 | Kallury et al. | |
| 8,114,660 B2 | 2/2012 | Pawliszyn | |

(Continued)

FOREIGN PATENT DOCUMENTS

| | | |
|---|---|---|
| CN | 200945379 Y | 9/2007 |
| EP | 2485035 A2 | 8/2012 |

OTHER PUBLICATIONS

EPA, Acid Digestion of Sediments, Sludges, and Soils, 1996, retrieved from internet: file:///C:/Users/xxu/Documents/e-Red%20Folder/15234694/epa-3050b.pdf.*

(Continued)

*Primary Examiner* — Xiaoyun R Xu
(74) *Attorney, Agent, or Firm* — Oblon, McClelland, Maier & Neustadt, L.L.P.

(57) ABSTRACT

A method for extracting an analyte in a sample is described. A sample and a solution in a microwave-extraction vial are microwave-heated and agitated. A vapor produced in the vial can be extracted into a liquid-phase medium contained in a porous membrane bag situated in the vial. The liquid-phase medium containing the vapor extract may then be analyzed for an analyte with gas chromatography-mass spectrometry.

20 Claims, 10 Drawing Sheets

(56) References Cited

U.S. PATENT DOCUMENTS

2013/0337477 A1   12/2013   Kuhr et al.
2015/0068291 A1    3/2015   Basheer et al.

OTHER PUBLICATIONS

Kumar, P.V., et al., "One-Step Microwave-Assisted Headspace Controlled-Temperature Liquid-Phase Microextraction for the Determination of Dichlorodiphenyltrichloroethane and its Main Metabolites in Aqueous Samples by Gas Chromatography with Electron Capture Detection", URL: http://research.nchu.edu.tw/upfiles/ADUpload/oc_downmul2339105941.pdf, National Chung-Hsing University, 28 Pages total, (Oct. 12, 2011).

Tsai, M., et al., "Analysis of Hexachlorocyclohexanes in Aquatic Samples by One-Step Microwave-Assisted Headspace Controlled-Temperature Liquid-Phase Microextraction and Gas Chromatography with Electron Capture Detection", Journal of Chromatography A, pp. 1891-1897, (2010).

Sarafraz-Yazdi, A., et al., "Liquid-Phase Microextraction", Trends in Analytical Chemistry, vol. 29, No. 1, 14 Pages total, (2010).

Ponnusamy, V.K., et al., "Microwave Assisted Headspace Controlled-Temperature Single Drop Microextraction for Liquid Chromatographic Determination of Chlorophenols in Aqueous Samples", URL: http://link.springer.com/article/10.1007%2Fs00604-012-0877-3, National Chung-Hsing University, 4 Pages total, (Aug. 14, 2012).

Spietelun, A., et al., "Green Aspects, Developments and Perspectives of Liquid Phase Microextraction Techniques", Talanta, vol. 119, pp. 34-45, (2014).

Pavón, J.L.P., et al., "Determination of Trihalomethanes in Water Samples: A Review", Analytica Chimica Acta, vol. 629, pp. 6-23, (2008).

\* cited by examiner

US 10,191,061 B2

MICROWAVE-ASSISTED HEADSPACE LIQUID-PHASE MICROEXTRACTION OF AN ANALYTE

CROSS REFERENCE TO RELATED APPLICATIONS

This application claims the benefit of priority from U.S. Provisional Application No. 62/207,756 filed Aug. 20, 2015, which is incorporated herein by reference in its entirety.

STATEMENT OF ACKNOWLEDGEMENT

This project was prepared with financial support by the King Abdul Aziz City for Science and Technology through the Science and Technology Unit at King Fand University of Petroleum and Minerals (project No. 10-WAT1396-04), as part of the National Science Technology and Innovation Plan.

BACKGROUND OF THE INVENTION

Technical Field

The present invention relates to a method of extracting an analyte from a sample using microwave-assisted headspace liquid-phase microextraction.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The Arabian Gulf area has undergone tremendous changes over the past decades in relation to management of water resources. According to recent estimations, daily production of desalinated water in gulf countries reached up to 23 million cubic meters, and Saudi Arabia produces a lion's share of it, which is 11 million cubic meters [Roberts, D. A., et al., Impacts of Desalination Plant Discharges on the Marine Environment: A Critical Review of Published Studies. *Water Res.* 2010, 44, 5117-5128—incorporated herein by reference in its entirety]. The contaminants produced during the desalination have been extensively reported in the literature. Desalination contaminants have impacted the marine ecological environment, and as a result their detectable concentrations were found in phytoplankton, invertebrates, and fish [Roberts, D. A., et al., Impacts of Desalination Plant Discharges on the Marine Environment: A Critical Review of Published Studies. *Water Res.* 2010, 44, 5117-5128; Lattemann, S., et al., Environmental Impact and Impact Assessment of Seawater Desalination. *Desalination* 2008, 220, 1-15—each incorporated herein by reference in its entirety]. Massive losses of coral, plankton, and fish in the Hurghada region of the Red Sea have also been attributed to desalination discharges [Hashim A., et al., Impact of Desalination Plants Fluid Effluents on the Integrity of Seawater, with the Arabian Gulf in Perspective. *Desalination* 2005, 182, 373-393; Mabrook, B. Environmental Impact of Waste Brine Disposal of Desalination Plants, Red Sea, Egypt. *Desalination* 1994, 97, 453-465—each incorporated herein by reference in its entirety]. However, there exist only a few reports on the impact assessment and bioaccumulation of disinfection byproducts in biota samples. For example, the Eastern Province of Saudi Arabia, where the world's largest water desalination plant is located, has not been evaluated to assess the impact of disinfection byproducts (DBPs) on biota. DBPs are unintentionally produced from the reactions of disinfectants with the natural organic matter in the water [Richardson, S. D., et al., Water Analysis: Emerging Contaminants and Current Issues. *Anal. Chem.* 2014, 86, 2813-2848—incorporated herein by reference in its entirety]. Many of the DBPs have been shown to cause cancer, and reproductive and developmental disorders in laboratory animals [Drinking Water Treatment, U.S. Environmental Protection Agency, EPA Document No. 810-F-99-013, Cincinnati, Ohio, 1999—incorporated herein by reference in its entirety]. They are also harmful to humans and are suspected carcinogens even at low parts per billion (ppb) concentration levels. Trihalomethanes (THMs) and haloketones (HKs) are among the most prevalent DBPs [Levesque, S., et al., Effects of Indoor Drinking Water Handling on Trihalomethanes and Haloacetic Acids. *Water Res.* 2006, 40, 2921-2930; Yang, X., et al., Factors Affecting Formation of Haloacetonitriles, Haloketones, Chloropicrin and Cyanogen Halides during Chloramination. *Water Res.* 2007, 41, 1193-1200—each incorporated herein by reference in its entirety]. For example, USEPA classified trichforomethane (TCM), bromodichloromethane (BDCM), and tribromomethane (TBM) as carcinogens, while chlorodibromomethane (CDBM) was listed as a possible carcinogen [Xu, X., et al., Percutaneous Absorption of Trihalomethanes, Haloacetic Acids, and Haloketones. *Toxicol. Appl. Pharmacol.* 2002, 184, 19-26—incorporated herein by reference in its entirety]. Some toxicological effects of HKs are also reported. More prominently, chromosornal aberrations are associated with trichloropropanone (TCP) [Blazak, W. F., et al., Activity of 1,1,1- and 1,1,3-Trichloroacetones in a Chromosomal Aberration Assay in CHO Cells and the Micronucleus and Spermhead Abnormality Assays in Mice. *Mutat. Res. Toxicol.* 1988, 206, 431-438—incorporated herein by reference in its entirety], and 1,1-dichloropropanone (DCP) has been reported to reduce cellular glutathione levels prior to cytotoxic effects [Merrick, B. A., et al., Chemical Reactivity, Cytotoxicity, and Mutagenicity of Chloropropanones. *Toxicol. Appl. Pharmacol.* 1987, 91, 46-54—incorporated herein by reference in its entirety]. Therefore, exposure to such compounds can lead to serious health implications.

The determination of various DBPs requires an efficient sample preparation method prior to chromatographic analyses. During the last two decades, different approaches of sample preparation have been reported for DBPs. Liquid-liquid extraction and solid phase extraction are commonly used conventional approaches [US Environmental Protection Agency. 1995 a Method 551.1: EPA-600/R-95/131. USEPA Office of Research and Development, National Exposure Research Laboratory, Cincinnati, Ohio; US Environmental Protection Agency. 2003 Method 552.3: USEPA Office of Ground Water and Drinking Water, Cincinnati, Ohio; Niri, V. H., et al., Fast Analysis of Volatile Organic Compounds and Disinfection by-Products in Drinking Water Using Solid-Phase Microextraction-Gas Chromatography/time-of-Flight Mass Spectrometry. *J. Chromatogr. A* 2008, 1201, 222-227—each incorporated herein by reference in its entirety]. These methods have many shortcomings, including consumption of large volumes of hazardous solvents, and furthermore, these time and labor-extensive extractions lead to low recoveries. Therefore, it is highly desirable to develop new extraction techniques for fast and accurate quantitation of trace level concentrations of DBPs in biological samples.

Microwave-assisted extraction (MAE) has a wide range of applications and overcomes many of the above-mentioned problems. It can be successfully applied to different biological samples such as plants and fish [Wang, S., et al., Design and Performance Evaluation of Ionic-Liquids-Based Microwave-Assisted Environmentally Friendly Extraction Technique for Camptothecin and 10-Hydroxycamptothecin from Samara of Camptotheca Acuminata. *Ind. Eng. Chem. Res.* 2011, 50, 13620-13627; Teo, C. C., et al., Development and Application of Microwave-Assisted Extraction Technique in Biological Sample Preparation for Small Molecule Analysis. *Metabolomics* 2013, 9, 1109-1128; Wang, H., et al., Dynamic Microwave-Assisted Extraction Coupled with Salting-out Liquid-Liquid Extraction for Determination of Steroid Hormones in Fish Tissues. *J. Agric. Food Chem.* 2012, 60, 10343-10351; Ma, Y., et al., Microwave-Assisted Extraction Combined with Gel Permeation Chromatography and Silica Gel Cleanup Followed by Gas Chromatography-Mass Spectrometry for the Determination of Organophosphorus Flame Retardants and Plasticizers in Biological Samples *Anal. Chim. Acta* 2013, 786, 47-53; Dong, S., et al., Four Different Methods Comparison for Extraction of Astaxanthin from Green Alga Haematococcus Pluvialis, *ScientificWorldJournal.* 2014, 2014, 1-7: Eskilsson, C. S., et al., Analytical-Scale Microwave-Assisted Extraction. *J. Chromatogr. A* 2000, 902, 227-250—each incorporated herein by reference in its entirety]. Minimizing the degradation of volatile and semi-volatile compounds, shortening the extraction time, lowering hazardous solvent consumption, and simplifying the entire operation are major advantages of MAE [Eskilsson, C. S., et al., Analytical-Scale Microwave-Assisted Extraction. *J. Chromatogr. A* 2000, 902, 227-250; Letelltei, M., et al., Influence of Sediment Grain Size on the Efficiency of Focused Microwave Extraction of Polycyclic Aromatic Hydrocarbons, *Analyst* 1999, 124, 5-14; Mandal, V., et al., Design and Performance Evaluation of a Microwave Based Low Carbon Yielding Extraction Technique for Naturally Occurring Bioactive Triterpenoid: Oleanolic Acid. *Biochem. Eng. J.* 2010, 50, 63-70; Ma, W., el al., Application of Ionic Liquids Based Microwave-Assisted Extraction of Three Alkaloids N-Nornuciferine, O-Nornuciferine, and Nuciferine from Lotus Leaf. *Talanla* 2010, 80, 1292-1297—each incorporated herein by reference in its entirety]. The combination of headspace extraction with MAE is an uncommon approach; however, to perform headspace extraction, instrumental modifications are required which makes it more tedious [Yeh, C.-H., et Headspace Solid-Phase Microextraction Analysis of Volatile Components in Phalaenopsis Nobby's Pacific Sunset. *Molecules* 2014, 19, 14080-14093—incorporated herein by reference in its entirety].

In view of the forgoing, one objective of the present disclosure is to provide a single step microwave-assisted headspace liquid-phase microextraction (MA-HS-LPME) method for the isolation and subsequent determination of analytes such as THMs and HKs in biota samples. In one aspect of this method, a PTFE ring is placed inside an extraction vial to support a solvent-containing porous membrane envelope or bag, and thus, no changes in the microwave instrument are required.

BRIEF SUMMARY OF THE INVENTION

According to a first aspect, the present disclosure relates to a method for extracting an analyte in a sample.

The method involves microwave-heating and agitating the sample and a solution in a microwave extraction assembly, which comprises a microwave extraction vial with a headspace portion and a bottom portion. The bottom portion optionally contains a stir bar, and the headspace portion contains a porous membrane bag. The porous membrane bag encapsulates a liquid-phase extraction medium. The sample and solution are located in the bottom portion of the microwave extraction vial and do not contact the porous membrane bag. The microwave-heating and agitating produces a vapor in the headspace portion.

The method also involves extracting the analyte from the vapor to produce a vapor extract within the liquid-phase extraction medium in the membrane bag.

In one embodiment of the method, the method also involves feeding the vapor extract to a gas chromatograph-mass spectrometer (GCMS) to detect and/or quantify the analyte.

In one embodiment of the method, the sample is derived from an organism that lives in a body of water.

In one embodiment of the method, the weight of the sample relative to the volume of the liquid-phase extraction medium is 0.04-100 g/mL.

In one embodiment of the method, the solution is an acid.

In one embodiment of the method, the solution is an acid, and the microwave-heating and agitating simultaneously digests the sample and extracts the analyte.

In one embodiment of the method, the acid is at least one selected from the group consisting of nitric acid, hydrochloric acid, hydrofluoric acid, sulfuric acid, and perchloric acid.

In one embodiment of the method, the sample comprises the analyte and an internal standard.

In one embodiment of the method, the porous membrane hag is positioned 1-10 cm above the sample.

In one embodiment of the method, the weight of the sample relative to the volume of the microwave extraction vial is 0.5-100 g/L.

In one embodiment of the method, the liquid-phase extraction medium is an organic solvent.

In one embodiment of the method, the liquid-phase extraction medium is an organic solvent which is at least one selected from the group consisting of benzene, cyclohexane, hexane, toluene, iso-octane, heptane, and decane.

In one embodiment of the method, the porous membrane bag comprises at least one polymer selected from the group consisting of polypropylene, polyethylene, nylon, polyvinylidene fluoride, and polyethersulfone.

In one embodiment of the method, the porous membrane bag comprises a porous membrane having a 10-200 µm wall thickness.

In one embodiment of the method, the microwave extraction assembly further comprises a ring within the headspace portion of the microwave extraction vial to support the porous membrane bag.

In one embodiment of the method, the sample and solution are microwave-heated to a temperature of 40-100° C.

In one embodiment of the method, the sample and solution are microwave-heated and stirred for 1-25 min.

In one embodiment of the method, the analyte is a trihalomethane or a haloketone.

In one embodiment of the method, the analyte is a trihalomethane or a haloketone and the trihalomethane or haloketone, the analyte is detected and/or quantified in the range of 0.02-200 ng per g of sample.

In a related embodiment, where the analyte is a trihalomethane or a haloketone, the trihalomethane is bromodichloromethane, tribromomethane, trichloromethane, dibromochloromethane, or combinations thereof, and the haloketone is 1,1-dichloro-2-propanone, 1,1-trichloro-2-propanone, or both.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
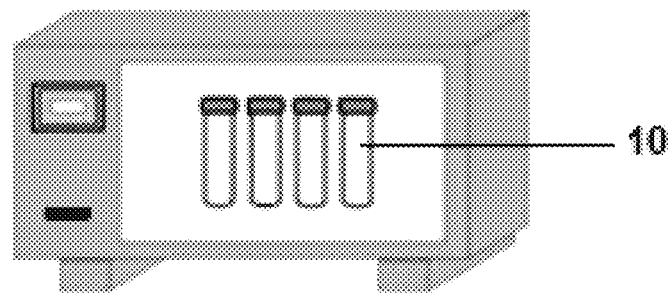
FIG. 1 is a microwave-heating source containing a microwave extraction assembly.

Embodiments of the present disclosure will now be described more fully hereinafter with reference to the accompanying drawings, in which some, but not all embodiments of the disclosure are shown.

The present disclosure will be better understood with reference to the following terms and meanings set forth below. Unless defined otherwise, all technical and scientific terms used herein have the same meaning as commonly understood to one of ordinary skill in the art.

According to a first aspect, the present disclosure relates to a method for extracting an analyte in a sample. The analyte may be an herbicide, a fungicide, a pesticide, a drug, a steroid, a microbial toxin, a metabolite, a disinfection byproduct, or some other small organic molecule. In one embodiment, the analyte may be a disinfection byproduct. As used herein, the term "disinfection byproduct" is a compound produced from the reaction of a water disinfectant with an organic impurity in an aqueous solution. Generally, the disinfection byproduct is a contaminant present in treated water or waste water that has been processed in a desalination plant, a water treatment plant, or a pool. Organisms exposed to the contaminants may sequester the disinfection byproducts in their tissues and organs. Disinfection byproducts may include iodoacetic acid, N-nitrosodimethylamine (NDMA), nitrogentrichloride, chloramine, halonitromethanes, haloacetonitriles, haloamides, halofuranones, nitrosamines, trihalomethanes, and haloketones. A preferred embodiment of the method relates to detecting and/or quantifying trihalomethanes and haloketones, more specifically, the trihalomethanes bromodichloromethane (BDCM) (I), tribromomethane (TBM, or bromoform) (II), trichloromethane (TCM, or chloroform) (III), and dibromochloromethane (DBCM) (IV), and the haloketones 1,1-dichloro-2-propanone (DCP) (V) and 1,1,1-trichloro-2-propanone (TCP) (VI).

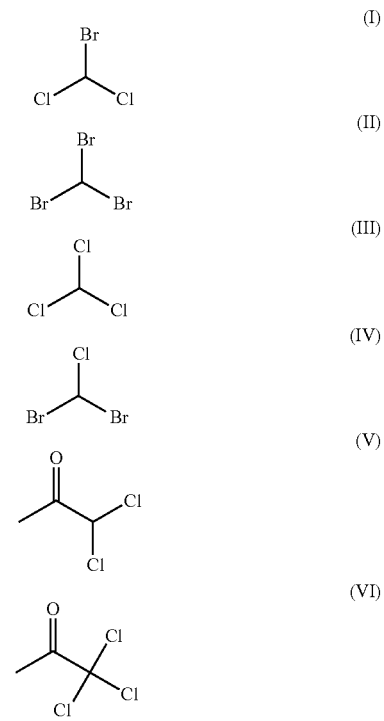

Another embodiment of the method is concerned with detecting and/or quantifying an analyte in a sample derived from an organism that lives in a body of water. For example, the organism may be a fish, an alga, a seaweed, a turtle, a dolphin, an echinoderm, a squid, a ray, an insect, or a crustacean, and the body of water may be an ocean, a bay, a river, a lake, a swamp, or a pond. A sample derived from an organism may be a piece of external tissue, such as a piece of skin, scale, or leaf, or an internal tissue such as a piece of muscle or liver, or the entire organism. In an alternative embodiment, the sample may be water taken from a body of water such as those mentioned previously, or from the processed water or wastewater of a water treatment plant, sewage treatment plant, or desalination plant. The sample may also be water taken from a treated artificial body of water, such as a pool, fountain, bath, aquarium, or hot tub. The sample may also be water taken from other natural environments such as groundwater and rainwater. The sample may contain one analyte, or it may contain more than one. Where the sample contains more than one analyte, the molar ratio between any two may range from 100:1 to 1:100, preferably 20:1 to 1:20, more preferably 5:1 to 1:5. In a preferred embodiment, the analyte is a disinfection byproduct.

Figure 2:
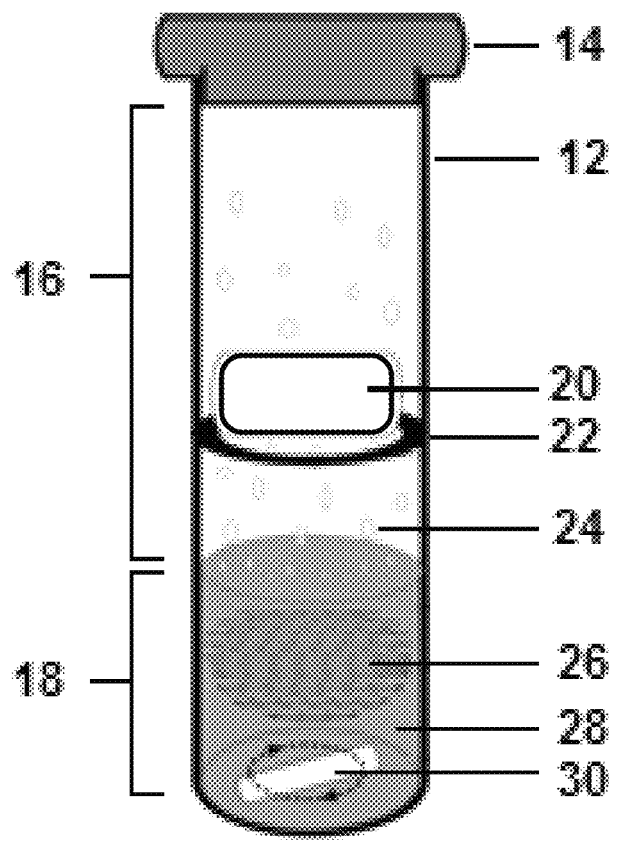
FIG. 2 is a microwave extraction assembly.

The method involves microwave-heating and agitating the sample and a solution in a microwave extraction assembly. FIG. 1 shows a microwave extraction assembly 10 inside a microwave-heating source. FIG. 2 shows an embodiment of a microwave extraction assembly. The microwave extraction assembly may comprise a microwave extraction vial 12 that may have a headspace portion 16 and a bottom portion 18. The bottom portion may comprise a sample 26 and a solution 28. The vial may comprise glass, ceramic, or polytetrafluoroethylene (PTFE) and have an interior volume of 20-300 mL, preferably 50-200 mL, more preferably 80-150 mL. The vial may have a round bottom, a flat bottom, or a pointed bottom, and may have side walls that are curved, sloped to the bottom, or straight up and down. In one embodiment, the weight of the sample relative to the volume of the microwave extraction vial may be 0.5-100 g/L, preferably 2-80 g/L, more preferably 10-60 g/L. The vial may also have a closure 14 in order to contain vapor and/or pressure produced by the microwave-heating, or the vial may be open to atmospheric pressure but topped by a vapor condenser. In a preferred embodiment, the vial is made of RITE and has a 100-125 mL volume with a closure.

The solution may include one or more of water, a salt solution, an organic solvent, a cell lysis reagent, or an acid. The salt of the salt solution may be sodium sulfate or sodium chloride. This organic solvent may have a dielectric constant of at least 5, preferably at least 10, more preferably at least 20 for efficient microwave-heating, and a boiling point of 50-100° C., preferably 60-90° C., more preferably 65-80° C. The organic solvent may be an alcohol, a polar aprotic solvent, a non-polar solvent, or mixtures thereof. Examples of alcohols include ethanol, methanol, and 2-propanol; examples of polar aprotic solvents include acetone, dimethyl sulfoxide (DMSO), acetonitrile, dimethylformamide (DMF), and ethyl acetate; examples of non-polar solvents include hexane, pentane, benzene, 1,4-dioxane, and diethyl ether. The organic solvent may be added to water, such as mixing ethanol and water. The organic solvent may be added to water to a 20-80 vol %, preferably 30-70 vol %, more preferably 40-60 vol % concentration relative to the water and organic solvent mixture. A cell lysis reagent may be present in the solution in order to disrupt the cell wall and/or cell membrane of a biological sample and release analyte. These reagents may be detergents such as sodium dodecyl sulfate andior Triton X-100, salts such as sodium chloride, potassium chloride, and/or ammonium sulfate, and/or a base such as sodium hydroxide and/or potassium hydroxide. In one embodiment, the solution comprises an acid, for example formic acid, benzoic acid, acetic acid, phosphoric acid, hydrobromic acid, hydroiodic acid, nitric acid, hydrochloric acid, hydrofluoric acid, sulfuric acid, and/or perchloric acid. Preferably the acid is nitric acid, hydrochloric acid, hydrofluoric acid, sulfuric acid, and/or perchloric acid; more preferably the acid is nitric acid.

In one embodiment, the sample may be mechanically processed prior to microwave-heating and agitating. This processing may lyse the cells of a biological sample, and may comprise sonication, extrusion, grinding, liquid homogenization, blending, scraping, slicing, centrifuging, drying, and/or freeze-thawing. In an alternative embodiment, cells of a biological sample may be ruptured by osmotic pressure.

In one embodiment, the concentration of the acid in the solution is 20 mM-1 M, preferably 50 mM-750 mM, more preferably 80-200 mM. A sufficient volume of acid may be added to total 0.1-1 mmol, preferably 0.2-0.8 mmol, more preferably 0.4-0.6 mmol acid per g sample.

In a preferred embodiment, the solution is 80-200 mM, or 90-120 mM, or about 100 mM nitric acid, and a sufficient volume is added to result in 0.45-0.55 mmol nitric acid per g of sample.

In an alternative embodiment where the sample may be processed water or a sample taken from a body of water, the solution may be omitted.

In one embodiment, the sample may comprise an internal standard. The internal standard may be present in the sample at a concentration of 0.02-200 ng, preferably 0.5-100 ng, more preferably 1-70 ng per g sample. The internal standard may be 1,2-dibromopropane, 2-benzoxalinone, 1-bromo-4-fluorobenzene, 1,1,1-trichloroethane, fluorobenzene, 4-bromofluorobenzene, trichloroethylene, 1,4-dichlorobenzene, and/or 1,2-dichlorobenzene. The internal standard may be a purified form of a previously mentioned disinfection byproduct that is known not to already exist in the sample. Or, the purified disinfection byproduct may be used as an internal standard in a sample that contains the same compound by using standard additions of the purified disinfection byproduct. Additionally, the internal standard may be another compound that has no interaction with the sample, solution, or existing analytes, in terms of adsorbing to the sample or reacting with other substances. Where an internal standard is added to a sample before undergoing extraction, the internal standard may show an extraction recovery of at least 80%, preferably at least 90%, more preferably at least 96%. The internal standard and an analyte of interest may have boiling points that differ by less than 40° C., preferably less than 30° C., more preferably less than 20° C. The internal standard may have similar partitioning properties compared with an analyte of interest. For example, where $K_{ow}$ is the octanol-water partition coefficient of a compound, the values of $\log(K_{ow})$ of an internal standard and an analyte of interest may differ by less than 2.0, preferably less than 1.5, more preferably less than 1.0. Preferably, though, the properties of the internal standard and analyte of interest are not so similar as to cause overlapping signals in the gas chromatogram or the mass spectra.

In one embodiment, the sample and solution are microwave-heated and stirred for 1-25 min, preferably 5-20 min, more preferably 10-15 min. The microwave power may be 10-1000 W, preferably 50-500 W, more preferably 80-300 W. The microwave radiation may be delivered to the bottom portion of the vial, or to the entire microwave extraction assembly. The microwave radiation may be delivered continuously, or intermittently. In one embodiment, the microwave-heating may increase the internal pressure of the microwave extraction vial. The internal pressure may be less than 40 bars, preferably less than 25 bars, more preferably less than 10 bars. In one embodiment, the sample may be heated to and maintained at a temperature of 40-100° C., preferably 60-90° C., more preferably 75-85° C. As shown in FIG. 1, a microwave-heating source may be able to accommodate more than one microwave extraction assembly, and thus, more than one extraction may be performed simultaneously. In an alternative embodiment, the sample may be heated first, and then stirred without additional heating.

In one embodiment, the sample is heated by a means other than microwave-heating, such as a hot water bath, a steam bath, a heat gun, a heating block, an oven, a wire heating element, an ultrasonicator, or by other non-microwave electromagnetic irradiation sources, such as an infrared laser. Additionally, the sample may be heated simultaneously by two heat sources, such as microwave radiation and a hot water bath. Alternatively, the sample may be preheated, such as in a hot water bath, prior to microwave-heating and agitating. The sample may be heated with a variable power to maintain a constant temperature, or the sample may be heated at a constant power with a variable temperature. The temperature of the sample may be inferred from a temperature probe placed in the bottom portion or the headspace portion of the vial, or on an exterior surface of the vial. In the embodiment where a bath or oven is used as a heating vessel, the temperature may be inferred from a temperature probe in the same heating vessel.

In one embodiment, the sample and solution are agitated by shaking, tilting, vortexing, or sonicating the vial, or by stirring the sample and solution with a stir bar, a stirring rod, or an impeller. Preferably, the sample and solution are stirred with a stir bar 30 located in the bottom portion of the vial. The stir bar may be stirred at a rate of 30-1000 rpm, preferably 60-700 rpm, more preferably 100-500 rpm. The ideal stirring rate may be the highest speed that agitates the sample and solution without splashing the sample and/or solution into the headspace portion, and this rate may depend on the type of sample, size of stir bar, and volumes of sample, solution, and microwave extraction vial. In one embodiment, the sample and solution are heated and stirred at rates that do not splash the sample and/or solution into the headspace portion by the formation of heated vapor bubbles.

The sample may react with the solution during the microwave-heating and agitating step. In an embodiment where the solution is an acid and the sample is derived from an organism, the acid may digest the cells of the sample and release an analyte or analytes contained in the sample. This acid digestion may be accelerated by the microwave-heating and/or agitating. Alternatively, the acid may be added and allowed to react with the sample prior to microwave-heating and agitating. The microwave-heating and/or agitating may cause molecules of sample, solution, analyte, anchor internal standard to evaporate from the bottom portion of the microwave extraction vial and enter the headspace as a vapor by diffusion and/or advection. In the embodiment where the sample comprises an analyte but not an internal standard, preferably the vapor comprises at least molecules of the analyte. In the embodiment where the sample comprises both an analyte and an internal standard, preferably the vapor comprises at least molecules of the analyte and the internal standard.

The vial also contains, in the headspace portion, a porous membrane bag that encapsulates a liquid-phase extraction medium. In one embodiment, this porous membrane bag may be located above and out of contact from the solution and sample by a separation of 1-10 cm, preferably 5-10 cm, more preferably 6-9 cm.

In one embodiment, the porous membrane of the porous membrane bag may comprise a polymer such as polypropylene, polyethylene, nylon, polyvinylidene fluoride, or polyethersulfone, preferably polypropylene or polyethylene, even more preferably polypropylene. In an alternative embodiment, more than one polymer may comprise the porous membrane. For example, the porous membrane may be composed of both polypropylene and polyethylene with a polypropylene to polyethylene weight ratio range of 1:10-10:1, preferably 1:5-5:1, more preferably 1:2-2:1.

In one embodiment, the porous membrane has a wall thickness of 10-200 µm, preferably 15-100 µm, more preferably 25-50 µm. The porous membrane may have a pore diameter of 0.04-0.80 µm, preferably 0.1-0.5 µm, more preferably 0.1-0.4 µm. The membrane may have a porosity of 40-90 vol %, preferably 50-85 vol %, more preferably 60-80 vol %. The liquid-phase extraction medium may fill 70-100%, preferably 80-100%, more preferably 90-100% of the pores exposed to the liquid-phase extraction medium from the interior of the membrane bag. Analyte contained in the headspace vapor may contact pores filled with liquid-phase extraction medium on the exterior of the membrane bag, partition into the medium n the pore, and diffuse into the bag as a vapor extract. Preferably, compounds in the sample or solution that are not of interest have low partitioning into the vapor and/or into the liquid-phase extraction medium in the pores, and thus do not appreciably form a vapor extract in the membrane bag. Preferably, the liquid-phase extraction medium and the vapor extract do not leak out of or evaporate from the membrane pores. The liquid-phase extraction medium may be prevented from leaking out of the bag by its surface tension and/or interaction with the membrane material. In an alternative embodiment, the liquid-phase extraction medium does not fill the pores of the membrane, but vapor is still able to diffuse through the pores and form a vapor extract within the membrane bag. In one embodiment, the membrane is pre-wetted with the liquid-phase extraction medium in order to fill the pores with the medium. In an alternative embodiment, the membrane is pre-wetted with a liquid phase that is a different compound than the liquid-phase extraction medium contained in the membrane bag.

The porous membrane bag may comprise more than one piece of membrane, for instance, the bag may comprise both an inner and outer membrane layer. Where the bag comprises more than one membrane, the membranes may be made of identical material. Alternatively, the membranes may be made of different material, have different thicknesses, and/or have different pore sizes.

The porous membrane bag may comprise a membrane in the shape of a tube, for example, a hollow fiber membrane, where the ends of the tube are closed in order to contain the liquid-phase extraction medium. The edges may be closed by an adhesive, a clamp, a tie, or by heat sealing. Alternatively, the membrane may form a balloon shape around the liquid-phase extraction medium, with the membrane closed at one side, or with the membrane edges tied at one point. Alternatively, the membrane bag may form a rectangular pillow shape around the extraction mediun this embodiment, the four edges may be sealed along each edge, or one edge may be a fold in the membrane with the remaining edges being sealed along each edge. In this pillow shape, the edges may measure 1-5 cm, preferably 2-4 cm, more preferably 2.2-3 cm in length, and the height may be 0.4-5 cm, preferably 0.8-4 cm, more preferably 0.8-2.8 cm.

In an alternative embodiment, the porous membrane bag is replaced by a single porous membrane layer that holds the liquid-phase extraction medium above the sample and solution. In another alternative embodiment, the porous membrane bag is replaced by a glass frit and/or supported by a glass frit that similarly holds the liquid-phase extraction medium above the sample and solution.

In another alternative embodiment, the liquid-phase extraction medium may be contained in the headspace in a smaller vial that has an opening covered by a porous membrane, which may allow for fragile membrane materials to be used in the microwave extraction assembly. This smaller vial may be supported in the headspace by any of the previously ways of supporting the porous membrane bag, or the smaller vial may be attached or built into an interior wall of the microwave extraction vial. The smaller vial may hold a volume of 0.05-5 mL, preferably 0.1-1 mL, more preferably 0.25-0.75 mL of the liquid-phase extraction medium. The smaller vial may have a cylindrical or conical shape, and may be positioned with the porous membrane on the top, side, or bottom. In the case where the liquid-phase extraction medium may leak through the membrane, the smaller vial may be positioned with the porous membrane on top. In one embodiment, the smaller vial is a tube with a porous membrane secured across both openings.

In one embodiment the liquid-phase extraction medium is an organic solvent, such as an alcohol, a polar aprotic solvent, a non-polar solvent, or mixtures thereof. Preferably the boiling point of the solvent or solvent mixture is greater than 50° C., preferably greater than 60° C., more preferably greater than 70° C., even more preferably greater than 80° C. Examples of alcohols that can be used as the liquid-phase extraction medium include ethanol, methanol, 1-propanol, and 2-propanol; examples of polar aprotic solvents include acetone, dimethyl sulfoxide (DMSO), acetonitrile, dimethylformamide (DMF), tetrahydrofuran (THF), and ethyl acetate; examples of non-polar solvents include hexane, cyclohexane, heptane, decane, benzene, 1,4-dioxane, iso-octane, n-octane, nonane, and toluene. Preferably the organic solvent is toluene, heptane, decane, iso-octane, or mixtures thereof. More preferably the organic solvent is toluene. The organic solvent may fill at least 95%, preferably at least 98%, more preferably at least 99% of the total pore volume of the portion of membrane exposed to the solvent. In an alternative embodiment, the extraction medium may be a solid-phase material, such as agarose, activated carbon, silica, alumina, magnesium silicate, or graphitized carbon black.

In one embodiment a single microwave extraction vial may comprise more than one porous membrane bag, each enclosing a different solvent and/or comprising a different type of membrane, for the purpose of extracting more than one type of analyte from the sample. Preferably, this embodiment may be used where two or more analytes in the sample have different partitioning characteristics with a single liquid-phase extraction medium. In this embodiment, different liquid-phase extraction media may be chosen to maximize the extraction efficiency of multiple analyte types.

In one embodiment of the method, the weight of the sample relative to the volume of the liquid-phase extraction medium is 0.04-100 g/mL preferably 0.5-50 g/mL, more preferably 1-20 g/mL.

The porous membrane bag may hold a volume of 0.05-5 mL, preferably 0.1-1 mL, more preferably 0.25-0.75 mL of the liquid-phase extraction medium. The membrane bag may enclose both the liquid-phase extraction medium and a gas. The gas may be present as a bubble or bubbles, and may comprise air, vaporized extraction medium, or any of the previously mentioned headspace vapor components. The gas may result from filling and/or sealing the membrane bag with liquid-phase extraction medium or it may be formed by heating the microwave extraction assembly. A gas in the membrane bag may comprise 0-50 vol %, preferably 0-10 vol %, more preferably 0-1 vol % of the total enclosed volume of the membrane bag.

The porous membrane bag may be supported in the vial by a screen, a mesh, or a ring placed inside the vial, or it may be supported by a protrusion attached to or integral with an inner wall of the vial. A ring, such as a rubber O-ring or a non-metallic washer, may be an advantageous support as it allows exposure of the membrane bag to vapors above and below in the headspace, and no modification to the microwave extraction assembly is required beyond positioning the ring. Thus, the microwave extraction assembly may comprise a standard laboratory microwave extraction vial without further alterations. Alternatively, the membrane bag may be supported from above, such as by a string attached or tied to the membrane bag. This string may be attached to an interior or exterior side of the microwave extraction vial, or it may be attached to the cap or closure of the microwave extraction vial. In a related embodiment, the membrane of the membrane bag may be directly attached to interior side of the closure or cap, such as by an adhesive or a clamp. Preferably, the membrane bag is supported by a ring placed inside the vial, and in one embodiment, this ring comprises PTFE.

The method also involves extracting the analyte from the vapor to produce a vapor extract within the liquid-phase extraction medium.

In one embodiment of the method, the extraction of the analyte occurs at the same time as the microwave-heating and agitating, which means that the entire extraction method occurs in a single operation. For example, an analyte can be extracted from a sample and into the headspace vapor, and from the vapor into the liquid-phase extraction medium, without requiring a researcher to perfoirn those extraction steps separately or subsequently. In addition, in the embodiment where the sample is derived from an organism and the solution is an acid, the acid digestion of the sample is also contained within the extraction operation, meaning that a separate sample preparation step such as cell membrane disruption is not required. Additionally, in this embodiment, parts of the analyte may be simultaneously partitioned to three locations within the microwave extraction vial: in the sample and solution in the bottom portion, in the vapor in the headspace portion, and within the liquid-phase extraction medium. In another embodiment, the analyte may be limited to different locations in the microwave extraction assembly throughout the method. For example, at the beginning of the heating and agitating step, the analyte may exist only in the bottom portion and in the vapor, without yet forming the vapor extract in the liquid-phase extraction medium. Similarly, for example, prolonged microwave-heating may completely vaporize the sample and solution, leaving the analyte in only the vapor and the vapor extract. Likewise, an internal standard may simultaneously exist in all three locations within the microwave extraction vial, or may be limited to one or two locations.

The amount of analyte or internal standard in the phases of the sample, solution, vapor, and liquid-phase extraction medium may depend on initial concentrations, the amount and rate of heating and agitating, and the partition coefficient of the analyte or internal standard among the different phases. Where two or more analytes are present, their relative concentrations may vary across different phases. Likewise, where one or more internal standards are present, the relative concentrations between an internal standard and an analyte, or between two internal standards, may also vary across different phases.

The method also involves feeding the vapor extract to a gas chromatograph-mass spectrometer (GCMS) to detect and/or quantify the analyte.

Following the vapor extraction, a vapor extract containing an analyte may be dissolved in the liquid-phase extraction medium. A syringe, cannula, or pipette may be used to puncture the membrane bag and withdraw a portion or all of its contents. In an alternative embodiment, the membrane bag may be placed into a solvent that dissolves the membrane while retaining the analyte. The liquid-phase extraction medium may be injected directly into a GCMS for analysis. Alternatively, the liquid-phase extraction medium may be diluted with an organic solvent or purified before injection into the GCMS.

In one embodiment, a typical commercial GCMS may be used. The carrier gas may be nitrogen, helium, and/or hydrogen. Preferably the carrier gas is helium with a purity of greater than 99.9 mol %, preferably greater than 99.99 mol %, more preferably greater than 99.999 mol %. The stationary phase of the gas chromatography column may be comprised of a methyl siloxane (also known as methyl polysiloxane or dimethyl polysiloxane), phenyl polysiloxane, dimethyl arylene siloxane, cyanopropylmethyl polysiloxane, and/or trifluoropropylmethyl polysiloxane with a film thickness of 0.10-7 μm, preferably 0.15-1 μm, more preferably 0.2-0.5 μm. The column length may be 10-120 m, preferably 15-50 m, more preferably 25-40 m, with an inside diameter of 0.08-0.60 mm, preferably 0.15-0.40 mm, more preferably 0.20-0.30 mm.

The parameters of a GCMS instrument and method of operation, including but not limited to flow rate, temperature, temperature gradient, run time, pressure, sample injection, sample volume, ionization method, ionization energy, and scanning range may be adjusted by a person of ordinary skill in the art to account for differences in samples, equipment, and techniques.

The analyte may be detected by monitoring a known elution time and/or m/z (mass to charge ratio) for a positive signal as compared with a blank sample. For BDCM, 83, 85, and 129 m/z may be monitored in the mass spectra; for TBM, 129, 173, and 252 m/z may be monitored; for TCM, 83 and 85 m/z may be monitored; for DBCM, 127, and 129 m/z may be monitored, for DCP, 127 m/z may be monitored; and for TCP, 161 m/z may be monitored. An internal standard's m/z may depend on its identity. The analyte may be quantified with a standard addition of an internal standard. Examples of internal standards were discussed previously. For quantitation, known concentrations of an internal standard may be added to a sample that is divided into aliquots. These aliquots are each extracted and measured by GCMS. Alternatively, aliquots of a vapor extract from a single trial could receive a standard addition. The linear response of the mass spectrometer counts per concentration of internal standard can be extrapolated to quantify an analyte. Additionally, more than one internal standard can be used in order to span a range of molecular masses. Alternatively, standards may be used to calibrate a GCMS prior to analyzing extracted samples.

In an alternative embodiment, gas chromatography may be used for detection and/or quantitation of an analyte without using mass spectrometry. In a related embodiment, the linear trend of the peak areas of the gas chromatogram may be used for quantitation. Generally, a person of ordinary skill in the art may be able to determine the procedure and calculations to quantify and/or detect an analyte based on GCMS data.

In one embodiment, the analyte is a trihalomethane or a haloketone. In another embodiment, the analyte is a trihalomethane or a haloketone, and may be detected and/or quantified in the range of 0.02-200 ng, preferably 0.5-100 ng, more preferably 1-70 ng per g sample. Trihalomethanes and haloketones may have different limits of detection (LOD, or signal at limit of detection, or $S_{LOD}$) and different limits of quantification (LOQ, or signal at limit of quantification, or $S_{LOQ}$), as defined by the equations $S_{LOD}=S_{RB}+3\sigma_{RB}$ and $S_{LOQ}=S_{RB}+10\sigma_{RB}$, where $S_{RB}$ is the signal of the reagent blank and $\sigma_{RB}$ is the standard deviation of the reagent blank. In one embodiment, TCM may have an LOD of at most 0.110 ng per g sample, preferably at most 0.10 ng/g, more preferably at most 0.02 ng/g, and an LOQ of at most 0.351 ng/g, preferably at most 0.2 ng/g, more preferably at most 0.02 ng/g; BDCM may have an LOD of at most 0.051 ng per g sample, preferably at most 0.04 ng/g, more preferably at most 0.02 ng/g, and an LOQ of at most 0.175 ng/g, preferably 0.10 ng/g, more preferably at most 0.02 ng/g; DCP may have an LOD of at most 0.085 ng per g sample, preferably at most 0.05 ng/g, more preferably at most 0.02 ng/g, and an LOQ of at most 0.263 ng/g, preferably at most 0.10 ng/g, more preferably at most 0.02 ng/g; DBCM may have an LOD of at most 0.069 ng per g sample, preferably at most 0.04 ng/g, more preferably at most 0.02 ng/g, and an LOQ of at most 0.213 ng/g, preferably at most 0.10 ng/g, more preferably at most 0.02 ng/g; TBM may have an LOD of at most 0.059 ng per g sample, preferably at most 0.04 ng/g, more preferably at most 0.02 ng/g, and an LOQ of at most 0.182 ng/g preferably at most 0.10 ng/g, more preferably at most 0.02 ng/g; TCP may have an LOD of at least 0.093 ng per g sample, preferably at most 0.05 ng/g, more preferably at most 0.02 ng/g, and an LOQ of at most 0.281 ng/g, preferably at most 0.10 ng/g, more preferably at most 0.02 ng/g.

The examples below are intended to further illustrate methods of microwave-assisted extraction of an analyte using a microwave extraction assembly and are not intended to limit the scope of the claims.

Example 1

Experimental Setup
Materials and Chemicals

A standard mixture of disinfection byproducts (DBPs) was obtained from Sigma Aldrich (Bellefonte, Pa., USA). This mixture contained THMs and HKs at 2000 μg mL$^{-1}$, which was prepared in methanol. Table 1 shows the physical properties of target compounds [Guidechem, "2-Propanone, 1,1-dichloro-513-88-2 properties reference," http://www.guidechem.com/reference/dic-4656.html#id_-1077596984; World Health Organization, "Trihalomethanes in Drinking-water, Background document for development of WHO Guidelines for Drinking-water Quality," http://www.who.int/water$_{13}$ sanitation_health/dwq/chemicals/en/trihalomethanes.pdf—each incorporated herein by reference in its entirety].

By appropriate dilution of the stock solution of DBPs in the same solvent, the working standard solutions were prepared on a daily basis. Required solvents were obtained from Supelco (Bellefonte, Pa., USA). Double deionized water was obtained from a Milli-Q system (Millipore, Bedford, Mass., USA). HNO$_3$ was obtained from Merck (Darmstadt, Germany). All glassware was washed with concentrated nitric acid, and then rinsed with deionized water and acetone, and then dried at 100° C. for 1 h in an oven. A porous polypropylene membrane (2.5 cm×2.5 cm with 0.03 mm wall thickness) was obtained from Membrana (Wuppertal, Germany).

TABLE 1

Physical properties of target compounds.

| Physical properties | TCM | TBM | DBCM | BDCM | DCP | TCP |
|---|---|---|---|---|---|---|
| Molecular weight (g mol$^{-1}$) | 119.38 | 252.73 | 208.28 | 163.8 | 126.96 | 161.41 |
| Solubility at 20-25° C. (g L$^{-1}$) | 7.5 | 3.1 | 1.0 | 3.3 | 6.3 | 7.4 |
| Boiling point ° C. | 61.3 | 149.5 | 119 | 90 | 117.3 | — |
| Vapor pressure at 20-25° C. (kPa) | 21.28 | 0.75 | 2.0 | 6.67 | — | — |
| Melting point ° C. | −63.2 | 8.3 | — | −57.1 | — | — |
| Density at 20° C. (g/cm$^3$) | 1.484 | 2.90 | 2.38 | 1.98 | 1.291 | — |
| log K$_{ow}$* | 1.97 | 2.38 | 2.08 | 1.88 | 0.20 | 1.12 |

*K$_{ow}$ is the octanol-water partition coefficient

GC-MS Analysis

Analyses were carried out using GC-MS (Shimadzu technologies, QP 2010 ultra system). An HP-1 methyl siloxane column (Shimadzu Rxi-5Sil MS; 30.0 m×0.25 mm×0.25 µm thickness) was used. The carrier gas was helium with high purity (>99.999%), and a constant flow of 1.0 mL min$^{-1}$ was used for analyzing samples. The following temperature program was used for the analyses: initial temperature of the column was 40° C., and it was held for 5 min, and then increased to 150° C. at 10° C. min$^{-1}$ and held for 5 min. The total run time was 21 min. The injection port, ion source, and interface temperatures were 200° C., 220° C., and 200° C., respectively. For qualitative determinations, the scan mode was operated from 50 to 550 m/z and for quantitative analysis selective ion monitoring mode was used.

Fish & Green Alga Samples

Fresh fish samples (Striped Red Mullet) were obtained from fish markets in Dammam, Eastern Province, Saudi Arabia. Fish samples were directly transferred to an icebox (−4° C.) for temporary storage before reaching the laboratory where they were stored at −18° C. prior to analysis.

Green alga samples were collected from the nearest desalination plant in Jabil, Eastern Province, Saudi Arabia, and then used in the experiments after being air dried.

MA-HS-LPWE Procedure

MA-HS-LPME experiments were carried out using a laboratory microwave extraction system (Anton Paar, Graz, Austria, software version v1.52) with 16 closed polytetrafluoroethylene (PTFE) vessels. The vessel's volume is 100 mL, and it can maintain a high temperature and pressure (240° C. and 40 bars).

Aqueous solutions are highly suitable for microwave digestion of biological samples, and tissues are easily digested by acidic or basic solutions [Chan, C.-H., et al., Microwave-Assisted Extractions of Active Ingredients from Plants. J. Chromatogr. A 2011, 1218, 6213-6225 incorporated herein by reference in its entirety]. 3 grams of biological samples were transferred to clean microwave vessels equipped with magnetic stir bars, 15 mL of 100 mM HNO$_3$ solution was added to each vessel. The membrane bag was filled with 500 µl of an organic solvent and heat sealed. This bag was suspended to certain depth in the microwave vessel via a PTFE ring. FIG. 2 shows a schematic for the setup used.

Example 2

Results and Discussion

MA-HS-LPME utilizes microwave energy for the fast heating of the solutions by the rotation of the molecules through the migration of ions and dipoles [Chan, C.-H., et al., Microwave-Assisted Extractions of Active Ingredients from Plants. J. Chromatogr. A 2011, 1218, 6213-6225—incorporated herein by reference in its entirety]. The efficiency of the extraction method is controlled by different experimental parameters, such as type of extraction solvent, depth of the membrane envelope inside microwave vessel, extraction temperature, sample weight, and extraction time.

Selection Action Parameters

Figure 3:
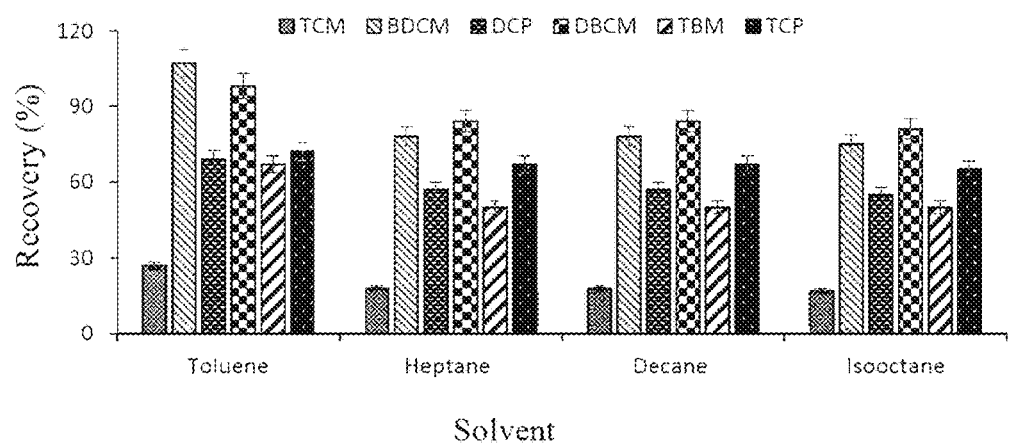
FIG. 3 is a graph showing the recoveries of the six disinfection byproducts (DBPs) interest when using four different solvents as the liquid-phase extraction medium.

The selection of solvent plays a major role in MA-HS-LPME. The dielectric constant and polarity of the solvent are important parameters to consider [Teo, C. C., et al., Development and Application of Microwave-Assisted Extraction Technique in Biological Sample Preparation for Small Molecule Analysis. Metabolomics 2013, 9, 1109-1128—incorporated herein by reference in its entirety]. Toluene, isooctane, heptane, and decane were selected as extraction solvents. FIG. 3 shows that toluene gave higher recoveries compared to other solvents. That is due to two reasons: the polarity of toluene and its higher dielectric constant, which when compared to other solvents is in following order: heptane<isooctane<decane<toluene [LSU Macromolecular Studies Group, "Dielectric Constant," http://macro.lsu.edu/HowTo/solvents/Dielectric%20Constant%20.htm—incorporated herein by reference in its entirety]. Thus toluene was selected as an ideal extraction solvent.

Figure 4:
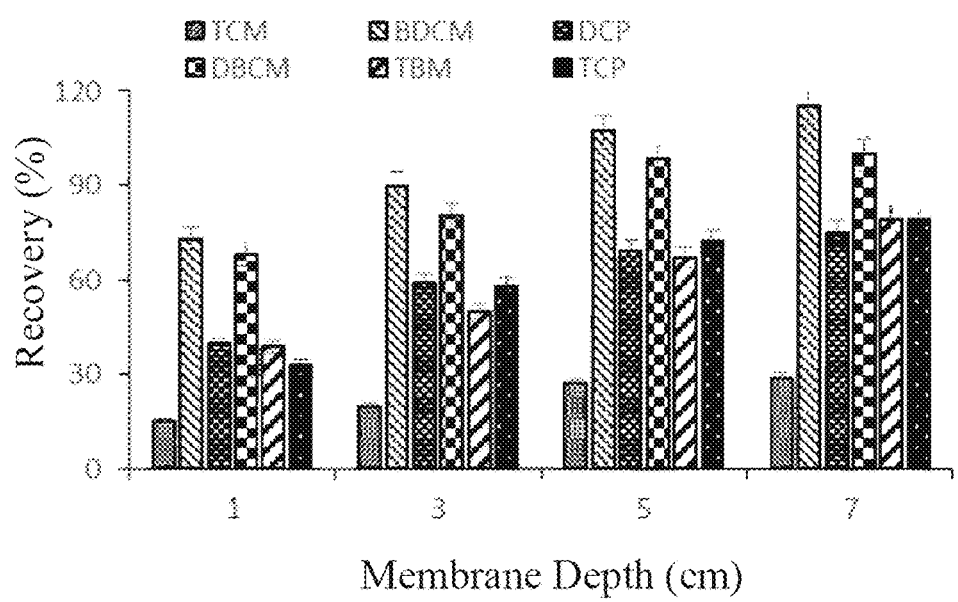
FIG. 4 is a graph showing the percent recoveries obtained for biological samples spiked with 20 ng of each DBP per g sample when the porous membrane bag has a different height (membrane depth) above the sample and solution.

Depth of the solvent-containing porous membrane was investigated in the range of 1-7 cm above the samples. FIG. 4 reflects the effect of membrane depth on the extraction efficiency of THMs and HKs. As it can be seen from FIG. 4, better extraction efficiency for all compounds was achieved at a depth of 7 cm. Interaction of the vapors with the liquid phase and disturbance created by stronger stirring at lower depths can reduce the extraction efficiency of MA-HS-LPME. But as the vessel represents a closed system, homogenous vapor formation occurs at all depths, so no significant differences were seen in the recovery of analytes.

Figure 5:
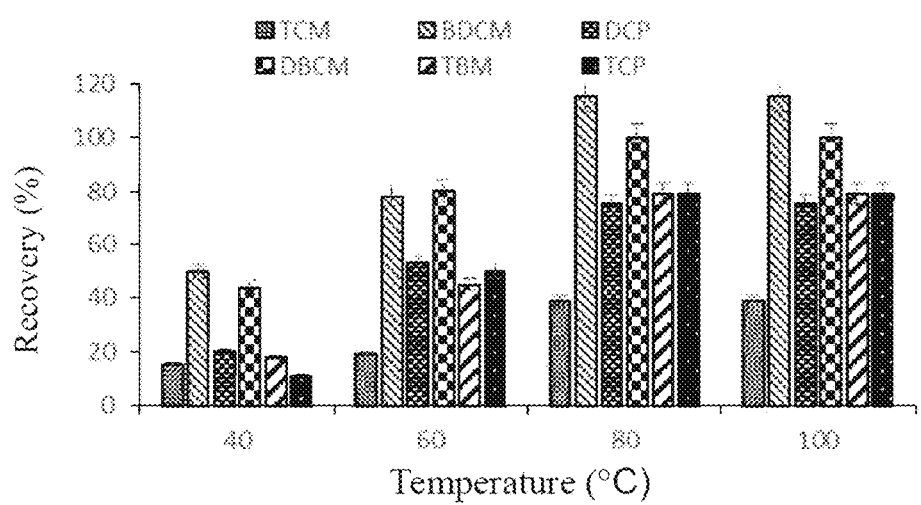
FIG. 5 is a graph showing the recoveries obtained for biological samples spiked with 20 ng of each DBP per g sample when the extraction is carried out at different temperatures.

The effect of the temperature on the extraction efficiency was evaluated between 40 and 100° C. FIG. 5 illustrates the recoveries of target analytes at different extraction temperatures. Recoveries were increased up to 80° C., and then leveled off. Temperatures below 80° C. were not enough to complete digestion of samples. By elevating the temperature, the extraction efficiency was improved. This increased extraction efficiency can be attributed to complete digestion of samples. However, at greater than 80° C., loss of solvent was observed. Thus, 80° C. was selected as the ideal temperature and used in further studies.

Figure 6:
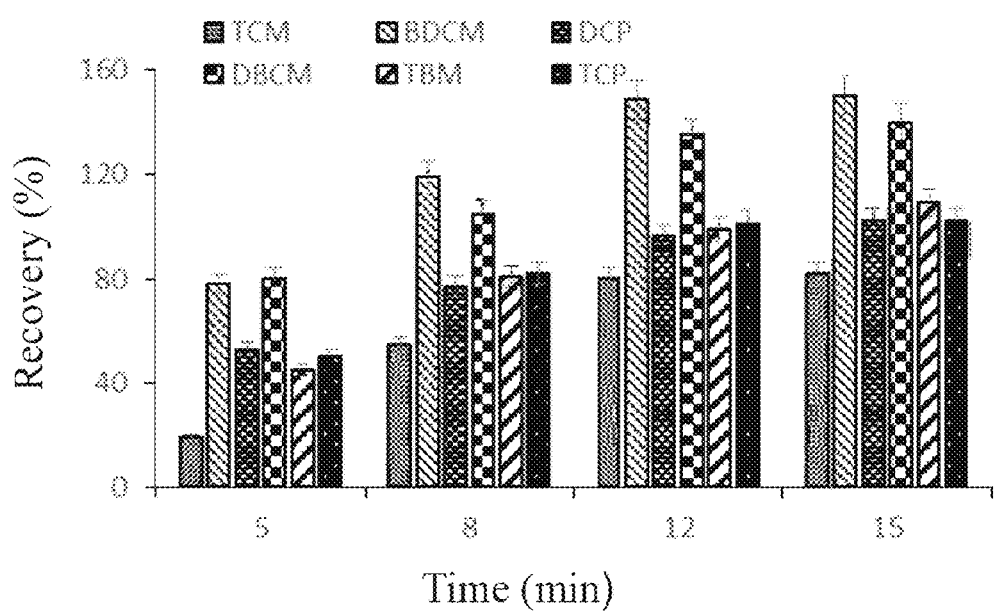
FIG. 6 is a graph showing the recoveries obtained for biological samples spiked with 20 ng of each DBP per g sample when the extraction is carried out for different lengths of time.

The effect of simultaneous extraction and digestion time was examined between 5 and 15 min. As it can be seen (FIG. 6), recoveries increased up to 12 min and no further additional increments were observed after this time. This observation shows that 12 min is sufficient to completely digest the sample and vaporize the analytes.

Figure 7:
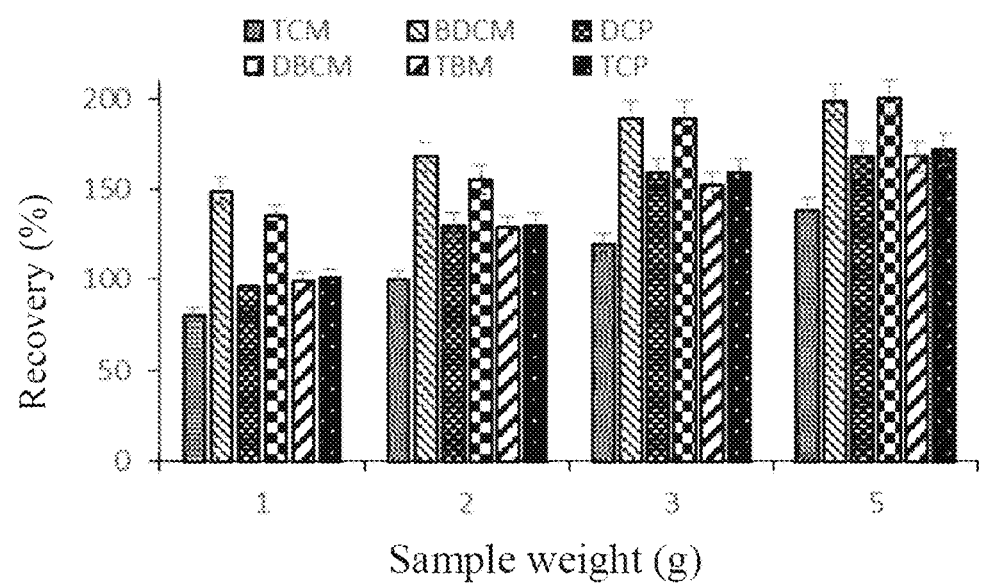
FIG. 7 is a graph showing the recoveries obtained for biological samples spiked with 20 ng of each DBP per g sample when different amounts of sample are used.

Different sample sizes (1-5 grams) were investigated to determine the ideal sample weight. FIG. 7 shows the influence of sample weight on recoveries of analytes. As it can be clearly seen, the recovery increases upon increasing the sample weight. However, we did not attempt more than 5 grams because it requires larger volumes of acid for digestion, which increases sample digestion time.

Method Validation and Performance

In order to assess the matrix effect and to ensure more accuracy, matrix-matched calibration curves were used in this work by using the sample matrix spiked with analyte standards. The regression equations were obtained by using 9 point standard concentrations (0.3, 0.5, 1, 5, 10, 20, 40, 70, 100 ng/g) as the abscissa and the related chromatogram peak areas as the vertical axis. It is presented in Table 2 that the linearity in the concentration range of 0.3-100 ng/g was good for brominated targets with 0.5-100 ng/g for the chlorinated ones with a determination coefficient ($R^2$) ranging from 0.9836 to 0.9954. The sensitivity of the proposed method was determined by measuring the limits of quantification (LOQ) and the limits of detection (LOD) of tested DBPs of the biota samples. Calculations were done according to the guidelines of the American Chemical Society's Committee on Environmental Analytical Chemistry and IUPAC, where $S_{LOQ}=S_{RB}+10\sigma_{RB}$ and $S_{LOD}=S_{RB}+3\sigma_{RB}$, and where $S_{LOQ}$, $S_{LOD}$, and $S_{RB}$ are the signal at the limit of quantification, at the limit of detection, and of the reagent blank, respectively, while $\sigma_{RB}$ is the reagent blank's standard deviation. The method LOQ was in the range from 0.175 to 0.351 ng/g while LODs of target analytes ranged from 0.051 to 0.110 ng/g. The relative standard deviations (RSDs) ranged between 1.1 and 6.8%. These results for the proposed method confirm that MA-HS-LPME is suitable for the analysis of THMs and HKs at trace levels in biological samples.

TABLE 2

Features of the MA-HS-LPME method.

| No. | DBPs | linear equation | linear range (ng/g) | $R^2$ | LODs (ng/g) | LOQs (ng/g) | % RSDs (n = 3) |
|---|---|---|---|---|---|---|---|
| 1 | TCM | y = 130.9x + 1476.1 | 0.5-100 | 0.9875 | 0.110 | 0.351 | 1.12 |
| 2 | BDCM | y = 180.49x + 3737.5 | 0.3-100 | 0.9887 | 0.051 | 0.175 | 3.64 |
| 3 | DCP | y = 59.129x + 404.19 | 0.5-100 | 0.9874 | 0.085 | 0.263 | 4.21 |
| 4 | DBCM | y = 140.5x + 6713.6 | 0.3-100 | 0.9836 | 0.069 | 0.213 | 2.11 |
| 5 | TBM | y = 1883.6x + 9939.4 | 0.3-100 | 0.9884 | 0.059 | 0.182 | 6.78 |
| 6 | TCP | y = 151.69x + 994.31 | 0.5-100 | 0.9954 | 0.093 | 0.281 | 5.43 |

Real Sample Analysis

Figure 8:
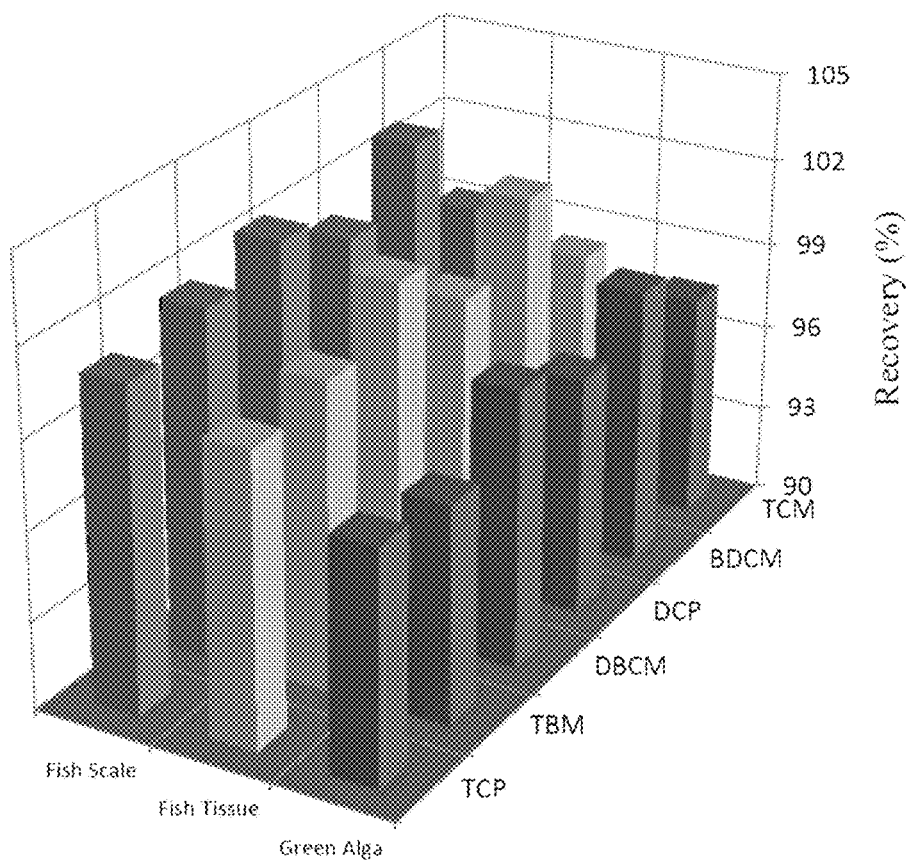
FIG. 8 is a graph showing the DBPs recoveries obtained for each type of biological sample spiked with 20 ng of each DBP per g sample.
Figure 9A:
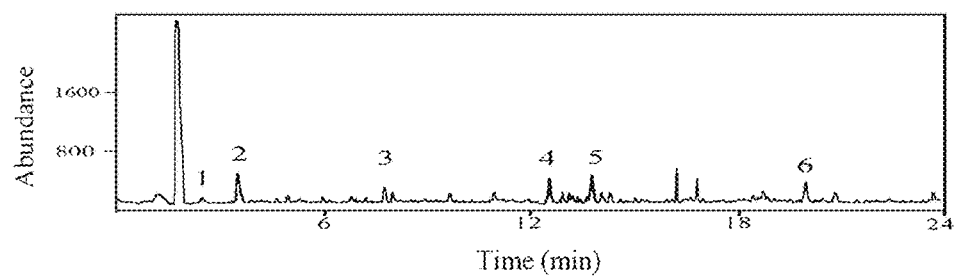
FIG. 9A is a GCMS chromatogram of DBPs extracted from fish scale samples.
Figure 9B:
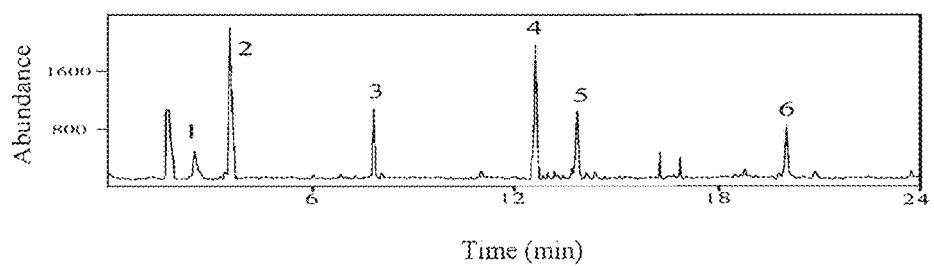
FIG. 9B is a GCMS chromatogramof DBPs extracted from fish scale samples that were spiked with 20 ng each DBP per g sample.

The developed MA-HS-LPME was applied for the detection of THMs and HKs in different biological samples. The previously deteirnined experimental conditions were used to quantitate DBPs in fish and green alga samples. The concentrations of target compounds that were detected are shown in Table 3. The results indicate that contents of THMs and HKs in biota samples collected from different regions of Saudi Arabia were below than USEPA allowed limits [EPA Advice Note on Disinfection By-Products in Drinking Water, Advice Note No. 4. Version 2—incorporated herein by reference in its entirety]. Fish scales have accumulated these compounds more than tissues because of direct and constant contact with the external contaminated environment [King. R. P., et al., Aquatic environment perturbations and monitoring: African experience, USA, 2003 166; Johal, M. S., et al., Sem study of the scales of freshwater snakehead Channa punctatus (Bloch.) upon exposure to endosulfan. Bull. Environ. Contam. Toxicol. 1994, 52, 7]8721—each incorporated herein by reference in its entirety]. To assess the effect of matrix, real samples were spiked with 20 ng/g of target analytes. FIG. 8 depicts the extraction recoveries which range from 97.4 to 102.5%. FIG. 9A and FIG. 9B present the GC-MS chromatograms of fish scale samples, unspiked and spiked, respectively, using the DSP labels from Table 2. Taken together, the chromatograms indicate no sample matrix interference using this method.

TABLE 3

Contents (ng/g) of the 6 analytes in the tested samples using MA-HS-LPME.

| samples | TCM | BDCM | DCP | DBCM | TBM | TCP |
|---|---|---|---|---|---|---|
| Fish scale | 3.0 | 5.2 | 3.1 | 5.2 | 4.9 | 3.5 |
| Fish tissue | 1.9 | 3.9 | 2.0 | 3.5 | 3.9 | 2.1 |
| Green alga | 0.9 | 2.9 | 1.8 | 3.0 | 2.5 | 1.9 |

MA-HS-LPME, a novel and efficient extraction method, was originally developed in this work. The feasibility of MA-HS-LPME was monitored by analyzing the trace level quantitation of trihalomethanes and haloketones in fish and green alga with GC-MS. Sample cleanup, extraction, and enrichment were done in one-step, which makes the sample preparation much simpler and faster. Advantageous conditions were as following: toluene as a solvent, membrane depth=7 cm, temperature=80° C., time=12 min, and sample weight=3 g. Low LODs, good linearity, and satisfactory recoveries were obtained. MA-HS-LPME was an effective technique in reducing the sample preparation time and solvent consumption. Microwave-assisted headspace liquid-phase microextraction can be applied to the extraction of other classes of disinfection byproducts from complex sample matrices.

The invention claimed is:

1. A method for extracting an analyte in a sample comprising:
    microwave-heating and agitating the sample and a solution in a microwave extraction assembly comprising:
      a microwave extraction vial with a bottom portion and a headspace portion and
      a porous membrane bag located in the headspace portion of the microwave extraction vial, said porous membrane bag encapsulating a liquid-phase extraction medium, wherein the sample and solution are disposed in the bottom portion, the porous membrane bag does not contact the sample and the solution, the porous membrane bag and the headspace portion are also subjected to the microwave-heating, and the microwave-heating and agitating produces a vapor in the headspace portion; and
    extracting the analyte from the vapor to produce a vapor extract within the liquid-phase extraction medium.

2. The method of claim 1, further comprising feeding the vapor extract to a gas chromatograph-mass spectrometer (GCMS) to detect and/or quantify the analyte.

3. The method of claim 1, wherein the sample is derived from an organism that lives in a body of water, and
    wherein the sample is a piece of external tissue, an internal tissue, or an alga.

4. The method of claim 1, wherein the weight of the sample relative to the volume of the liquid-phase extraction medium is 0.04-100 g/mL.

5. The method of claim 1, wherein the solution is an acid.

6. The method of claim 5, wherein the microwave-heating and agitating simultaneously digests the sample and extracts the analyte.

7. The method of claim 5, wherein the acid is at least one selected from the group consisting of nitric acid, hydrochloric acid, hydrofluoric acid, sulfuric acid, and perchloric acid.

8. The method of claim 1, wherein the porous membrane bag is positioned 1-10 cm above the sample.

9. The method of claim 1, wherein the weight of the sample relative to the volume of the microwave extraction vial is 0.5-100 g/L.

10. The method of claim 1, wherein the liquid-phase extraction medium is an organic solvent.

11. The method of claim 10, wherein the organic solvent is at least one selected from the group consisting of benzene, cyclohexane, hexane, toluene, iso-octane, heptane, and decane.

12. The method of claim 1, wherein the porous membrane bag comprises at least one polymer selected from the group consisting of polypropylene, polyethylene, nylon, polyvinylidene fluoride, and polyethersulfone.

13. The method of claim 1, wherein the porous membrane bag comprises a porous membrane having a 10-200 μm wall thickness.

14. The method of claim 1, wherein the microwave extraction assembly further comprises a ring within the headspace portion of the microwave extraction vial to support the porous membrane bag.

15. The method of claim 1, wherein the sample and solution are microwave-heated and stirred for 1-25 min.

16. The method of claim 1, wherein the analyte is a trihalomethane or a haloketone.

17. The method of claim 2, wherein the analyte is a trihalomethane or a haloketone, and the trihalomethane or haloketone is detected and/or quantified in the range of 0.02-200 ng trihalomethane or haloketone per g of sample.

18. The method of claim 16 wherein the trihalomethane is bromodichloromethane, tribromomethane, trichloromethane, dibromochloromethane, or combinations thereof, and the haloketone is 1,1-dichloro-2-propanone, 1,1,1-trichloro-2-propanone, or both.

19. The method of claim 1, wherein the liquid-phase extraction medium is confined within the porous membrane bag.

20. The method of claim 1, wherein the porous membrane bag is supported in the microwave extraction vial by a screen or a mesh placed inside the microwave extraction vial, or is supported by a protrusion attached to or integral with an inner wall of the microwave extraction vial.

* * * * *